United States Patent [19]

Cooper

[11] 4,252,594
[45] Feb. 24, 1981

[54] X-RAY PATIENT SUPPORT STRETCHER AND METHOD FOR FABRICATION

[75] Inventor: Adrianus A. G. Cooper, Alliance, Ohio

[73] Assignee: The Babcock & Wilcox Company, New Orleans, La.

[21] Appl. No.: 309

[22] Filed: Jan. 2, 1979

Related U.S. Application Data

[63] Continuation of Ser. No. 829,401, Aug. 31, 1977, Pat. No. 4,145,612.

[51] Int. Cl.³ .................... B29C 17/00; B29D 9/04
[52] U.S. Cl. ....................... 156/285; 250/439 R; 264/510; 264/571; 428/106
[58] Field of Search ............... 250/439 R, 451, 456; 264/510, 571; 156/285, 286; 428/106

[56] References Cited

U.S. PATENT DOCUMENTS

| 3,575,756 | 4/1971 | Maus | 156/286 |
| 3,666,600 | 5/1972 | Yoshino | 264/510 |
| 3,730,820 | 5/1973 | Fields et al. | 428/106 |
| 3,897,345 | 7/1975 | Foster | 250/439 |
| 3,947,686 | 3/1976 | Cooper et al. | 250/439 |
| 4,145,612 | 3/1979 | Cooper | 250/456 |

Primary Examiner—William R. Dixon, Jr.
Attorney, Agent, or Firm—Robert J. Edwards; Robert H. Kelly

[57] ABSTRACT

A patient support stretcher for X-ray units is formed by curing a multiple layered composite in situ on a balsa wood core.

1 Claim, 2 Drawing Figures

U.S. Patent  Feb. 24, 1981  4,252,594
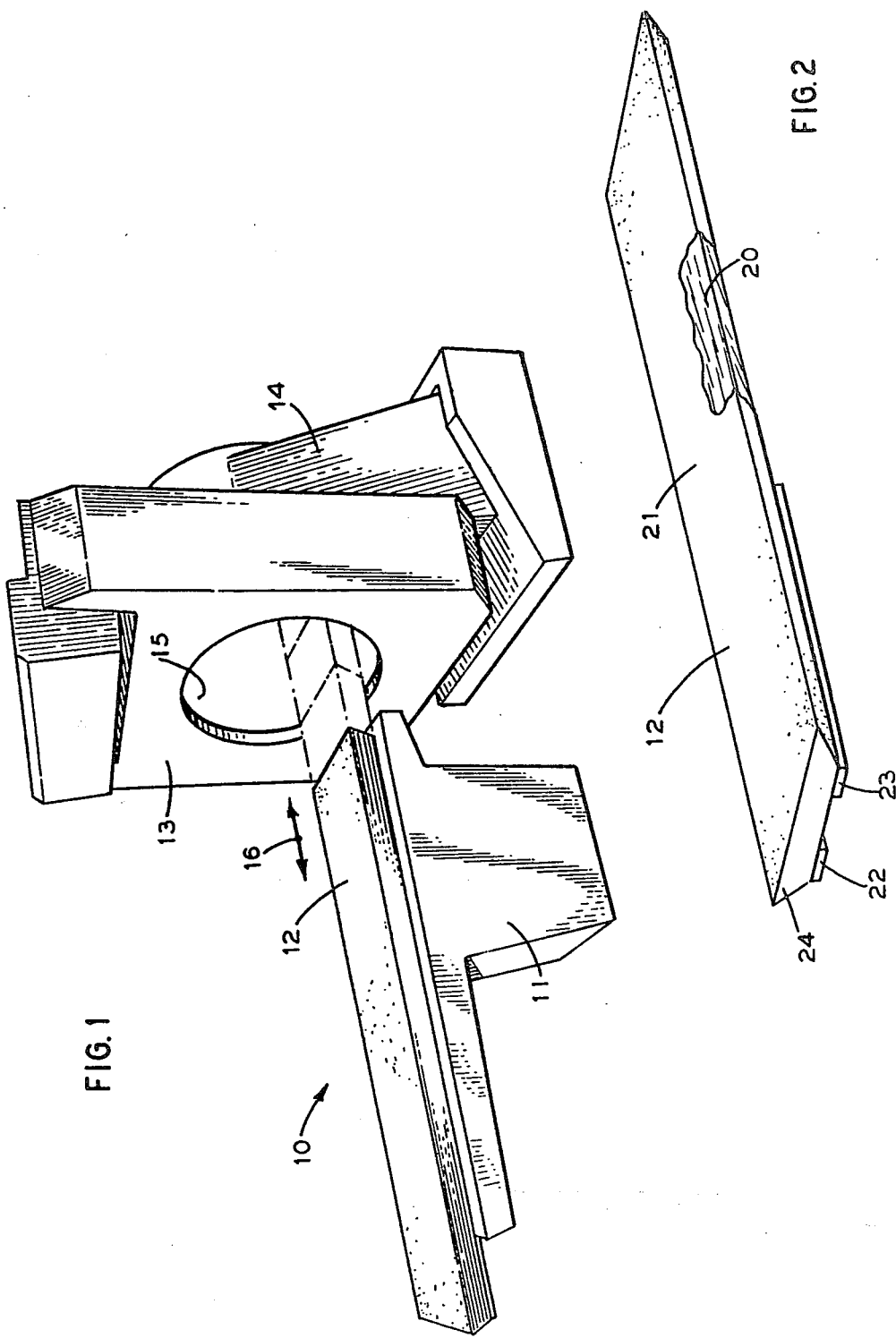

X-RAY PATIENT SUPPORT STRETCHER AND METHOD FOR FABRICATION

This is a continuation of application Ser. No. 829,401 filed Aug. 31, 1977 now U.S. Pat. No. 4,145,612.

BACKGROUND OF THE INVENTION

The present invention relates to a composite patient support stretcher used to support patients during X-ray examinations, and, more particularly, to a polymeric resin strengthened fibrous shell with a balsa wood core support structure, and a method for forming the same.

The increasing application of X-ray medical procedures in lieu of such invasive techniques as surgery for examination, diagnosis or therapy, and the development of tomographic procedures (wherein X-rays of a predetermined plane section are made) to fulfill objectives which are unobtainable by conventional radiographical procedures have promoted the usage of accessory X-ray equipment having characteristics particularly suited for a specific application.

In conventional radiology, for example, the patient is subjected to radiation from an X-ray tube acting as a point source. The attenuation of the rays (reduction of power per unit area with distance from the source) through the thickness of the patient's body is recorded on a single film. Because it is desirable to limit the radiation dose (radiation per unit volume of body tissue), it is important to reduce the attenuation attributable to accessory equipment, such as patient support stretchers, which is interposed within the X-ray path, in order to reduce the required source intensity. Thus, a patient support as shown in U.S. Pat. No. 3,947,686 is described as having low X-ray attenuation (equivalent to 1 mm Al or less), in addition to minimal deflection under load when supported in a cantilevered position. The support therein is formed with a polyurethane foam core and a shell composed of graphite fiber embedded in polyurethane. For convenience the shells may be fabricated from prepregs. Prepregs are pre-engineered, ready to mold combinations of resin and reinforcement. U.S. Pat. No. 3,897,345 also describes a patient support designed for low attenuation purposes which is composed of a shell containing graphite or carbon fibers in a plastic resin matrix around and bonded to a rigid polyurethane core. Moreover, British Pat. No. 1,435,223 discloses the use of panels composed of cast resin reinforced with carbon fiber material that has a hard foam core sandwiched between the panels in an apparatus for subjecting a patient to X-ray or gamma-ray examination or therapy. The apparatus is characterized as having considerable mechanical strength, and low X-ray and gamma-ray absorption.

The shells of the prior art patient support stretchers are typically cured in a mold prior to bonding with the foam cores since application of the shell curing heat may be detrimental to the foam, particularly where polyurethane is used. The shells are subsequently bonded to the core. Thus, a multi-phase labor intensive procedure is required to form the stretchers, that is, separately molding the top shell and the bottom shell; trimming the shells; shaping the core; bonding the core to the bottom shell; and, bonding the top shell to the core-bottom sheel combination.

Since irregularities in stretcher density can appear as images on conventional radiographic photographs, allowable density variations are stringently limited in order to preclude interpretation thereof as a tumor.

Recently, tomographic procedures have been developed to provide images that reveal information which may be hidden from view in conventional radiographic diagnosis due to overlap of anatomical features. In computerized tomography, for example, an image of a cross-sectional plane of a specimen is developed by sequentially directing X-rays through the subject from a plurality of directions. In the basic scanning process, a collimated X-ray beam passes through the patient's body (and at some angles through the stretcher), is attenuated to varying degrees, and impinges on a sensor which detects the amount of radiation received and electronically converts it to a signal that may be recorded by a computer. Angular rotational movement of the radiation source is coordinated with that of the sensor. The patient typically is translated normal to the orbital plane defined by the rotation of the source-sensor pair. The X-ray profiles of each section are processed by the computer which can reconstruct the images that have been accumulated to depict cross sections of the body.

Sine tomographic techniques are not as sensitive to density variations as conventional radiographic techniques, the stretcher does not require precision density homogeneity. Moreover, because the X-ray beam is well collimated, only the sections being scanned are irradiated and overall dose received for a complete scan of the section is comparable to the dosage received from a single conventional X-ray. Thus, the significance of low patient support stretcher attenuation is less critical than in conventional radiography. The combination of these factors is conducive to the use of core materials having medium attenuation but which can be more efficiently fabricated.

SUMMARY OF THE INVENTION

In accordance with the present invention, an X-ray patient support stretcher is provided with a balsa wood core covered by a multiple layered composite containing fiber strrengthened polymeric resin.

A method is disclosed wherein the shell is concurrently cured and bonded in situ with the balsa wood core.

The various features of novelty which characterize the invention are pointed out with particularity in the claims annexed to and forming a part of this specification. For a better understanding of the invention, its operating advantages and specific objects attained by its use, reference should be had to the accompanying drawings and descriptive matter in which there is illustrated and described a preferred embodiment of the invention.

BRIEF DESCRIPTION OF THE DRAWINGS

In the accompanying drawings, forming a part of this specification, and in which reference numerals shown in the drawings designate like or corresponding parts throughout the same, FIG. 1 is a perspective view of an X-ray scanning unit and X-ray table; and FIG. 2 is a perspective view, partly broken away, of a patient support stretcher made in accordance with the invention.

DESCRIPTION OF THE PREFERRED EMBODIMENTS

FIG. 1 illustrates a tomographic X-ray scanning unit, generally indicated by reference numeral 10, and an X-ray table 11 having a longitudinally extendable radiolucent patient support stretcher 12. The X-ray scanning unit contains a scanning apparatus 13 rotatably mounted to a base member 14. The scanning apparatus 13 is provided with an opening 15 of sufficient size to accommodate a patient (not shown) lying prone upon the support stretcher 12.

As is best shown in FIG. 2, the patient support stretcher 12 is generally composed of a core material 20 to which a skin 21 is adhered. In the preferred embodiment, the core material is balsa wood and the skin is a laminate of multi-layered composite composed of prepregs with fibers in a polymeric resin material.

In the preferred embodiment, support rails 22, 23 are appended to the lower side of the patient support oriented parallel to the longitudinal axis of the stretcher 12. The support rails 22, 23 are received within channels (not shown) of the X-ray table 11 for translating 16 the stretcher 12 and patient through the opening 15 of the scanning apparatus 13. Other well known means may be used in lieu of the support rails 22, 23 for longitudinally extending the patient support stretcher. End plates 24 (only one of which is shown) cover the ends of the core.

The skin 21 includes a plurality of layers of oriented fibers in polymeric matrices that are sandwiched between a fabric prepreg impregnated with a polymeric resin to form the skin. The polymeric resin used in the skin could be an epoxy or a polyester. The fibers could be carbon, graphite or a fiber sold under the trademark Kevlar. For example, layers of Narmco T300/5213, which is an epoxy matrix containing graphite fibers, produced by Narmco Materials, Inc., Costa Mesa, Calif., were sandwiched between a prepreg, also made by Narmco, known as 181 style Kevlar 49/5213, which is prepreg containing Dupont's Kevlar 49 fiber woven in fabric form and impregnated with an epoxy resin. Kevlar is a high tensile modulus (higher than $8 \times 10^6$ psi), high tensile strength (higher than $3.5 \times 10^5$ psi) aramid fiber. An aramid fiber may be described as a manufactured fiber in which the fiber-forming substance is a long-chain synthetic polyamid in which at least eighty-five percent of the amid linkages are attached directly to two aromatic rings. Some properties of Kevlar 49 in fabric style 181 are illustrated in Table I.

TABLE I

| | |
|---|---|
| Density (lb in.−3) | .047 |
| Tensile Strength (kpsi) | 75 |
| Tensile Modulus (Mpsi) | 4.7 |
| Compressive Strength (kpsi) | 27 |
| Compressive Modulus (Mpsi) | 4.5 |
| In-plane Shear Strength (kpsi) | 16 |
| In-plane Shear Modulus (Mpsi) | .3 |

The skin 21 need not be formed continuously about the core. Moreover, in operation the stresses in the top portion of the patient support will be predominantly tensile stresses, and those in the bottom of the stretcher compressive. Hence, in the preferred embodiment, the skin 21 is formed with separate and distinct top and bottom laminates or skins, each designed with fiber orientations to accommodate the predominant stresses, respectively, in the top and bottom of the stretcher.

The number of layers or plies of composite used to form the laminate are determined by the amount of attenuation allowable, and the required strength and stiffness of the resulting patient support stretcher. The use of the fabric containing aramid fibers such as those marketed as Kevlar, to surface the composite results in a scratch resistant patient support surface. Moreover, the fabric increases the strength of the stretcher in the width direction, thereby increasing the stretcher's capability to withstand handling forces during installation and during patient positioning.

Due to the fact that the thermal expansion and contraction of the fabric is different from that of the unidirectional plies the fabric on the core side of the laminate is needed to make the laminate balanced and symmetrical, thereby minimizing nonsymmetry of the thermal stresses when the laminate cools off after curing. Nonsymmetry of the stresses can cause the delamination of the laminate or its separation from the core of both.

Instead of or in combination with the unidirectional graphite fibers, unidirectional aramid fibers could be used in the topskin where the stresses are predominantly tensile stresses. Since the compressive properties of Kevlar are substantially less than the tensile properties, the use of unidirectional aramid fibers is not advantageous in the bottom skin, where the stresses are predominantly compressive stresses.

Aramid fiber is less expensive than graphite or carbon, it has approximately the same X-ray attenuation and tensile strength but has a lower elastic modulus. Use of aramid fibers may therefore be advantageous where large deflections of the stretcher are acceptable.

The characteristic properties of balsa wood, the lightest wood commercially available, allow selection of a composite and core system that are not adversely affected by temperatures detrimental to the foam cores of the prior art. Hence, the patient support stretcher 12 may be formed by concurrently curing the skin in situ while bonding to the balsa wood core 20. This eliminates the steps of pre-molding the skin, and subsequently bonding the pre-molded skin to the core.

In order to form the patient support stretcher, a balsa wood core is cut to the desired shape. The wood core is sealed typically with a resin component which is compatible with the polymeric resin in the skin prepregs.

In the preferred embodiment, top and bottom support stretcher skins are laid up and cured consecutively, forming lap joints where they meet on each side of the stretcher. A prepreg consisting of the aramid fiber fabric impregnated with a polymeric resin is applied to the balsa wood core such that one group (weave) of the interwoven fibers in the fabric is oriented in parallel with the length of the stretcher. Multiple layers of prepregs containing resin with oriented fiber aligned parallel to the longitudinal axis of the stretcher are then layered on the stretcher, followed by a final layer of the described aramid fiber prepreg. The components are then subjected to conventional vacuum bag molding techniques and cured, in order to cause the plies of composite to laminate and bond to the balsa wood core.

It will be evident to those skilled in the art that additional changes may be made without departing from the scope of the claimed invention.

The embodiments of the invention in which an exclusive property or privilege is claimed are defined as follows:

1. A method for forming a radiolucent patient support stretcher of the type having a balsa wood core, and a composite skin with multiple layers of oriented fibrous reinforcement in polymeric matrices sandwiched between resin impregnated fabrics which comprises the steps of applying a first layer of resin impregnated fabric onto the balsa wood core, applying the multiple layers of oriented fibers in the resinous matrices onto the first layer of fabric with the oriented fibers arranged parallel to the length of the core, applying a second layer of resin impregnated fabric onto the multiple layers of fibrous reinforced polymeric matrices, and vacuum bag molding and curing the composite skin to the balsa wood core in situ.

* * * * *